US008871186B2

(12) United States Patent
Pronovost et al.

(10) Patent No.: US 8,871,186 B2
(45) Date of Patent: Oct. 28, 2014

(54) COMPOSITIONS AND METHODS FOR CONTROL OF MALODOR AND OTHER ENVIRONMENTAL CONTAMINANTS

(71) Applicant: Red Lion Chem Tech, LLC, San Diego, CA (US)

(72) Inventors: Allan D. Pronovost, San Diego, CA (US); Michael E. Hickey, Escondido, CA (US)

(73) Assignee: Red Lion Chem Tech, LLC, San Diego, CA (US)

( * ) Notice: Subject to any disclaimer, the term of this patent is extended or adjusted under 35 U.S.C. 154(b) by 0 days.

(21) Appl. No.: 13/784,389

(22) Filed: Mar. 4, 2013

(65) Prior Publication Data
US 2014/0056837 A1 Feb. 27, 2014

Related U.S. Application Data

(60) Provisional application No. 61/691,720, filed on Aug. 21, 2012.

(51) Int. Cl.
| | | |
|---|---|---|
| *A61L 9/014* | (2006.01) | |
| *A61K 8/26* | (2006.01) | |
| *A61K 33/06* | (2006.01) | |
| *A61Q 15/00* | (2006.01) | |
| *A01N 59/06* | (2006.01) | |
| *A61K 8/02* | (2006.01) | |
| *A61K 8/25* | (2006.01) | |
| *A61Q 19/10* | (2006.01) | |
| *A61Q 11/00* | (2006.01) | |

(52) U.S. Cl.
CPC .............. *A61L 9/014* (2013.01); *A61K 8/0204* (2013.01); *A61Q 19/10* (2013.01); *A61K 33/06* (2013.01); *A61K 2800/56* (2013.01); *A61K 8/26* (2013.01); *A61K 8/25* (2013.01); *A01N 59/06* (2013.01); *A61Q 15/00* (2013.01); *A61Q 11/00* (2013.01)
USPC ........... 424/68; 424/76.6; 424/68.4; 424/76.1

(58) Field of Classification Search
None
See application file for complete search history.

(56) References Cited

U.S. PATENT DOCUMENTS

| | | | |
|---|---|---|---|
| 4,949,672 A | 8/1990 | Ratcliff et al. | |
| 5,094,190 A | 3/1992 | Ratcliff et al. | |
| 5,176,108 A | 1/1993 | Jenkins et al. | |
| 5,267,531 A | 12/1993 | Appel et al. | |
| 5,382,571 A | 1/1995 | Granger et al. | |
| 5,762,023 A | 6/1998 | Carter | |
| 5,826,543 A | 10/1998 | Raymond et al. | |
| 5,970,915 A | 10/1999 | Schlueter et al. | |
| 6,098,569 A | 8/2000 | Kent et al. | |
| 6,216,634 B1 | 4/2001 | Kent et al. | |
| 6,296,841 B1 | 10/2001 | Schneider | |
| 6,319,342 B1 * | 11/2001 | Riddell | 156/62.4 |
| 6,405,677 B2 | 6/2002 | McPherson et al. | |
| 6,622,658 B2 | 9/2003 | McPherson et al. | |
| 6,667,030 B1 | 12/2003 | Schneider | |
| 6,743,420 B2 | 6/2004 | Schneider | |
| 6,794,350 B2 | 9/2004 | Johansen et al. | |
| 6,962,129 B1 | 11/2005 | Lawson | |
| 6,987,099 B2 | 1/2006 | Trinh et al. | |
| 7,037,475 B2 | 5/2006 | Dokter et al. | |
| 7,270,814 B2 | 9/2007 | Xu et al. | |
| 2003/0133990 A1 * | 7/2003 | Hursey et al. | 424/601 |
| 2003/0235605 A1 | 12/2003 | Lelah et al. | |
| 2006/0034935 A1 | 2/2006 | Pronovost et al. | |
| 2012/0048285 A1 | 3/2012 | Mishra et al. | |

FOREIGN PATENT DOCUMENTS

WO    WO-00/23120    4/2000

OTHER PUBLICATIONS

Reider. Endocytic adaptors-social networkng at the plasma membrane. 2011.*
International Search Report and Written Opinion issued in PCT/US13/56059, mailed Jan. 29, 2014, 10 pages.

* cited by examiner

*Primary Examiner* — Scott Long
*Assistant Examiner* — Sarah Alawadi
(74) *Attorney, Agent, or Firm* — Morrison & Foerster LLP

(57) ABSTRACT

Nanocomposite compositions forming mixed clathrates and methods for using such compositions for entrapping guest moieties such as malodors, molds and cells are disclosed.

7 Claims, No Drawings

COMPOSITIONS AND METHODS FOR CONTROL OF MALODOR AND OTHER ENVIRONMENTAL CONTAMINANTS

CROSS-REFERENCE TO RELATED APPLICATION

This application claims priority from U.S. Ser. No. 61/691,720 filed 21 Aug. 2012. The content of this document is incorporated by reference herein in its entirety.

TECHNICAL FIELD

The invention relates to nanocomposite compositions comprising self-assembling mixed clathrates and methods of using the same for remediation of malodors and other contaminants. More particularly, it concerns, for example, sequestering chemical malodor components, such as those generated by the biological processes associated with living organisms, with the invention compositions.

BACKGROUND ART

There is a variety of environmental contaminants that are candidates for removal by the invention methods and compositions. Among these are odoriferous compounds with undesirable odors (malodors), organism contaminants such as molds and mildew, algae, spores, and the like.

Malodorous chemical compounds, all of which are in need of proper odor control technology, are classified in several ways which can include description of the malodor, common malodor name, chemical name, and/or the chemical formula. Malodorous compounds are classified as being primary odor causing agents comprising basal chemical structures (or functional groups), or secondary odor causing agents as the result of decay.

An example of primary odor causing agents of concern include: urine based malodors, comprised of ammonia ($-NH_3$), or urea ($NH_2CONH_2$); putrid odors comprised of volatile fatty acids (R—COOH or derivatives including acetic acid, propanoic acid, butyric acid, isobutyric acid, valeric acid, isovaleric acid, 2-ethyl butyrate, or ethanol); rotten egg odors comprising mercaptans (X—SH); total reduced sulfur compounds such as hydrogen sulphide ($H_2S$), methyl mercaptan ($CH_3S$—H), dimethyl sulphide ($CH_3$—S—$CH_3$) and dimethyl disulphide ($CH_3$—S—S—$CH_3$); fermenting perspiration odors comprised of diacetyl (2,3-butanedione, $C_4H_6O_2$); fecal odors comprised of skatole (3-methyl-1H-indole, $C_9H_9N$); skunk odor comprised of tert-butyl mercaptan (2-methyl-2-propanethiol, $C_4H_{10}S$); rancid cheese, sweat, putrid odors comprised of isovaleric acid (3-methylbutanoic acid, $C_5H_{10}O_2$); onion odor comprised of methional (3-methylthio), propionaldehyde, ($C_4H_8OS$); rotten fish odor comprised of trimethylamine (N,N-dimethylmethanamine, $C_3H_9N$); garlic odor comprised of allicin (2-propene-1-sulfinothioic acid S-2 propenylyester, $C_6H_{10}OS_2$); and sour putrid odor comprised of pyridine ($C_5H_5N$), to name a few.

Secondary odor causing agents include: putrid odors comprised of putrescine (diaminobutane, $C_4H_{12}N_2$); cadaver odor comprised of cadaverine (1,5-diaminopantene, $C_5H_{14}N_2$); among others too numerous to mention but incorporated here by reference.

There is almost an unlimited number of primary and secondary odor causing agents many more than those listed above. This is especially true for secondary odor causing compounds owing their diversity to the flux of decay upon decomposition. There is the continued transition of odoriferous compounds as a result of decay. The number, type, and complexity of odoriferous compounds are further complicated by the potential dynamic transition of malodor from solid to liquid to gaseous form over time. The dynamic transition may be attributable to changes in the state of matter due to physical factors such as temperature or pressure, due to biological factors such as enzymatic or microbial breakdown, or due to entropic decay.

Most malodorous compounds, however, have the ability to hydrogen bond as part of their molecular structure with few exceptions. Hence, malodors, as such, have a nearly universal ability to form this type of association and this affords the means to bond malodors through this functionality no matter their shape, size, chemical composition or molecular weight. This ability is retained independent of the molecular diversity attributable to the flux of decay over time. Malodorous compounds, as such, may occur in either solid, liquid or gaseous forms and compounds may readily transition from one state of matter to another as part of the spontaneous decomposition of matter during molecular decay. This makes molecular recognition difficult from a mimetic standpoint in that the end-product of decay is a moving molecular target.

The simplest and most common approach for dealing with a malodor is to mask it by introducing a new odor stronger than the malodor. The result is an increase in the overall odor level but frequently both odors are discernible. The effect is short lived and the malodors still can be readily detected.

Another general approach for malodor control is to use chemical oxidation using materials such as sodium hypochlorite, chlorine dioxide, chloramine-T, hydrogen peroxide, sodium percarbonate or potassium permanganate are used to oxidize odoriferous compounds. The presumption with this approach is that the compounds involved in malodor are oxidizable. For example, U.S. Pat. Nos. 6,667,030; 6,743,420; and 6,296,841 disclose the use of compounds based on N-sodium, N-chloro-para-toluene-sulfonamide and N-sodium, N-chloro-para-benzenesulfonamide (e.g., chloramine-T) to neutralize certain malodorous materials. This is limited to mercaptans, sulfides, and amine-based compounds. In another example, Clorox Corporation employs odor locking mineral crystals (e.g., borates), along with fragrances, as an additive to bentonite clay in a formulation for cat litter (U.S. Pat. Nos. 4,949,672; 5,094,190; 5,176,108).

Oxidizing agents used to oxidize malodorous compounds tend to be very harsh; dangerous to use and are often incompatible with fabrics due to bleaching effects. Oxidation of malodors generally requires that the oxidizing agents be used at high concentration, but high concentrations of oxidizing agents such as chloramine-T can be harmful to fish, animals, people and the environment in general. Furthermore, use of oxidizing agents to control malodors provides a temporary solution at best, if it is even an effective solution at all.

A common variant of chemical oxidation for gaseous malodor compound control involves ozonation. Ozone emitting devices are commonly available for household and industrial use and involve the oxidation of chemical species with ozone free radicals, but high levels of ozone are known to be toxic to humans and animals upon prolonged exposure and cause cellular degeneration of mammalian tissue over time.

Absorption with bulk absorbents is another passive process that involves the uptake of liquids which may contain soluble odoriferous compounds. The bulk absorbent composite materials may be any material or structure that readily imbibes water. These can include fibers, clays, moisture absorbing polymers, or any liquid absorbing material or combinations. Absorption affords no specificity or selectivity or affinity for odoriferous compounds and their absorption is merely the result of being in solution as the solvent is absorbed. Odoriferous materials can desorb or leech out of the bulk absorbent over time due to evaporation wherein the malodor persists.

Another method used for removal of specific primary malodors is the physical absorption and possible temporary sequestration of the malodorous compound within the pores of a medium such as charcoal. The uses of adsorbents that will imbibe malodorous materials by ion exchange are somewhat more effective but none are non-reversible or universally binding in nature. Examples of adsorbents include the Zorbitex™ technology of OIL-DRY Corp. of America/Combe, Inc., activated carbon is used as the basis for the Odor Eaters™ technology used for foot odor control, and the triple technology used for cat litter which involves the use of odor blocking with activated carbon, use of super adsorbent polymers and the use of Arm & Hammer baking soda. The adsorption process is readily reversible and does not actively neutralize or chemically bond the odoriferous chemical species. In addition, all malodorous compounds are not able to be adsorbed. Adsorption is a selective process and limited to specific primary molecules only.

Materials like activated charcoal and some naturally occurring or synthetic aluminosilicates are often used because they physically absorb liquids or gases and dissolved lower molecular weight primary malodor molecules. Absorption is temporary due to desorption. Following physical absorption as liquid or gas, odor compounds may remain temporarily sequestered within their pores due to the nominal pore size and tightness of fit. Some molecules may potentially interact with the pore surface through weak Van der Waals forces. Adsorption materials are usually structured as large granular or pellet form so as to provide a structural mesoporous framework for harboring molecules. Pores serve as physical compartments to temporarily hold molecules. Examples include the treatment of bentonite clay with starch polymers, or polymers or agents in order to reduce dust or aid in clumping as found in U.S. Pat. Nos. 5,267,531; 5,762,023; and 5,826,543 as assigned to Nestle Purina. Another example includes the use of oil free corn germ granules as corn-based cat litter (U.S. Pat. Nos. 6,098,569; 6,216,634; 6,405,677; and 6,622,658). These adsorptive media become readily saturated and require regeneration.

Adsorption, even with weak Van der Waals force interactions, is generally a secondary characteristic of materials like activated carbon or zeolites and is dependent upon the specific structure of the molecular pore in the material. As the attraction for malodorous compounds is mostly absorption dependent, often times to help enhance the pore penetration of the adsorbing materials such as zeolite, the adsorbing materials may be pre-loaded with a surrogate molecule or ion, e.g., a cation or anion, as a means to induce ion exchange. This, however, requires a liquid environment. Consequently this approach is only partially effective for odor removal as most malodors are generally comprised of larger organic molecules and do not occur as solitary primary elemental molecules or as ionized chemical species. The approach does have some limited odor control application with small odoriferous molecules such as ammonia, hydrogen sulfide, etc.

The notable exceptions wherein adsorbents may be effectively utilized are industrial applications for hydrogen sulfide, dimethyl disulfide, dimethyl sulfide, methyl mercaptan, or sulfur dioxide removal from gaseous or liquid streams as used in pulp mills or petroleum processing. Adsorbents like activated carbon or activated alumina, however, exhibit "avalanche" effects as activated carbon beds readily fill up with entrapped species. Spent adsorbents can be recycled to remove entrapped molecules but the end products of regeneration create disposal problems of their own. A good example of this is the multi-acre recycled sulfur ponds, which are known environmental and community problems. Adsorbent materials, although they are designed specifically for the adsorption of certain low molecular weight primary malodors with application in industrial processes such as liquid or gas stream cleaning in the petroleum industry; are often misused when applied to general odor absorption. These general use applications are generally outside the scope of utility for adsorbents and the adsorbents are merely functioning as absorbents as they have a porous structure, like a sponge. Utility as such does not imply effectiveness.

The physical absorption feature exhibited by absorptive or adsorptive media can also be used as the basis for filtration, another process used for the temporary retention of odoriferous materials in liquid samples. This process is most commonly used in waste-water treatment.

The inherent problem with adsorption, absorption, and or filtration is that they are passive processes that involve no intermolecular bonding and are fully reversible based on the environmental conditions. Hence these processes do not remove malodors, per se, but hide them for a period of time, either until the media is saturated or until evaporation sets in. These are only effective as true adsorbents, with defined chemical species such as ammonia, or hydrogen sulfide and only under specific chemically engineered conditions. They are also totally ineffective against high MW malodorous compounds. Adsorbents can be effective only with odors found in the liquid or gaseous state but not in the solid state.

Another method for malodor control attempts to neutralize the malodor through interaction with another chemical, such as a salt, for example sodium bicarbonate, sodium hydrogen carbonate, phosphate salts, or esters of phosphoric acid, isomorphous double salts that are hydrated sulfates of univalent cations (e.g., potassium, sodium, ammonium, cesium, or thallium) or trivalent cations (e.g., aluminum, chromium, manganese, cobalt, or titanium) commonly referred to as alum, to neutralize the malodor. Prohibitively massive quantities of chemical salt would be required to stoichiometrically neutralize all the odor molecules, which is not practical relative to the application. This process is reversible, making it only temporary, and its effectiveness is limited to the mass of the chemisorbing species. So, in spite of neutralization, the malodors return. For example, sodium bicarbonate (U.S. Pat. No. 6,962,129; Church and Dwight) is used routinely to neutralize odors, but as noted above, reactions are reversible allowing malodors to return and require large quantities of chemical to be used with any efficacy. The neutralized chemical also needs to be removed and can become pasty in applications if it becomes wet. The neutralization approach is limited to certain types of odor compounds, provided they are chemically compatible, and thus it cannot be applied to all gaseous malodors and is generally ineffective against non-gaseous odors with the noted exception of transient interaction.

Another method infrequently used for malodor control is counteraction. This involves the use of two odors (one malodorous and one not) which when brought into proximity of each other (but not mixed) result in a temporary reduction of the overall odor. This process is termed neutralization or neutral scent when no odor results and reodorization when a milder, more pleasant odor replaces the malodor. This process involves pairs of odorants that neutralize each other's respective odors through the utilization of Zwaardemaker conjugates. This process is the basis for some consumer products. Counter-reactants are malodor specific and different formulations are required for sulfur-based odors, nitrogen-based odors, and other common cooking odors. Effectiveness of those counter-reactants can be enhanced through use of electrostatic polymers and viscosity modifiers.

A more recent approach has been the use of enzymatic compounds to attempt to enzymatically cleave the malodorous compounds to render them ineffective. These enzymes are only effective on certain protein or carbohydrate-based odors. Enzymes are used to cleave protein, carbohydrate, or lipid based material to yield non-odoriferous compounds. The action of these materials is limited as their functional groups are narrowly selective with limited cleavage specificity and each enzyme can be costly not only to develop, but to produce. The requirement exists that the sample must contain a malodor compound for which the enzyme has specificity. Examples include lysostaphin (U.S. Pat. No. 6,794,350), the enzyme-based product of America's Preferred, Inc. Specialty Chemical Products (Santa Ana, Calif.), or the use of carbohydrate oxidase U.S. Pat. No. 7,270,814), among others. Enzymes are readily inactivated by surfactants or germicides and trace quantities found in shampooed carpets renders this method ineffective.

The natural processes of enzymatic and microbial breakdown are involved in accelerated decay. These processes are part of natural decomposition but the decay process takes time and is slow. During decay a variety of malodorous compounds are released in solid, liquid, and gaseous form. Although the end result of accelerated decay is decomposition, malodorous compounds are the major by-product over time. It is the by-products of decay that are particularly malodorous and most difficult to get rid of as the by-products are composed of diverse high molecular weight organic compounds not easy to identify, treat, or eliminate due to their molecular complexity and diversity over time as the result of entropic decay and flux.

Another method for malodor control has been passive molecular entrapment. As example, cyclodextrin is a soluble ring-like structure composed of six to twelve glucose molecules. The ring-like structure of cyclodextrin is open on both sides similar in concept to a bowl without a bottom or top. It has been promoted for use to absorb any molecule that would fit into the ring. U.S. Pat. No. 6,987,099, for example, refers to the use of non-complexed cyclodextrin compositions with primary application on fabrics. The molecule has no ability to permanently bind or entrap any molecule that is absorbed into the ring structure. Any absorption is coincidental at best wherein the probability of absorption or desorption is 50/50 at best. Weak electrostatic interactions may play a part. U.S. Pat. No. 6,987,099 notes that small molecules are not sufficiently absorbed by cyclodextrin molecules because the cavity of the ring structure is too large to adequately hold smaller malodorous compounds like ammonia, and the ring structure is too small to adequately hold larger malodorous compounds found in human perspiration. Also pointed out is that cyclodextrin, as a food source, readily supports the growth of microorganisms especially in aqueous environments. Hence, cyclodextrin has to be used in conjunction with antimicrobials and surfactants in order to reduce growth of microorganisms and to promote passive entrapment of molecules capable of being temporarily held in the ring structure. The need to use cyclodextrin in a sterile environment greatly limits its use, as malodorous environments are riddled with microbes.

Numerous attempts have been made to increase the absorption and retention of molecules in the open ring structure of cyclodextrin and have included the use of cyclodextrin at high solute concentrations (in spite of its solubility limit of 1.85%), use of mixtures of cyclodextrin to achieve overall soluble concentrations up to 20%, use of anti-microbial agents, use of cyclodextrin compatible surfactants, use of salts, humectants, and/or perfumes. Presumably, if cyclodextrin were indeed effective at odor removal, it would be effective on scents and perfumes as well, which it is not. Although the material has been promoted as being effective in odor removal, in reality it is a soluble material that is ineffective in and of itself. In some instances, it may augment malodor masking through temporary entrapment, giving it minimum effectiveness at best.

Malodors are generally caused by the presence of organic compounds, such as those containing thiol or amine functionalities, or inorganic compounds such as sulfur, sulfur dioxide, or nitrogen dioxide, and are typically generated by the standard biological processes of living systems, such as excretory processes or decomposition of organic matter. Malodors may occur in liquid, solid, or gaseous form, and malodorous chemicals are diverse in terms of size, physical properties, structural features, and they change in both molecular size and diversity over time during decay Silica-based compositions for odor control have been described, for example, in U.S. Pat. Nos. 5,970,915 and 7,037,475. These publications teach the use of underived silica gel, which functions as a desiccant, thus trapping water along with any polar odor molecules dissolved therein.

Inclusion compounds have received some use as delivery vehicles for sanitizing agents. Applications have utilized preformed inclusion compounds as partial clathrates as the means for delivering a deodorizing agent (as a guest moiety) which is subsequently released from the temporary inclusion compound to sanitize and indirectly treat odors but have not been used for malodor control wherein the malodor is the guest moiety. U.S. Pat. No. 5,382,571 describes the use of preformed clathrates of peroxyacids as the guest moiety. (Although called a clathrate, these moieties would more correctly chemically be called inclusion compounds in that the guest moiety is not fully enclosed and a full cage structure is not utilized.)

In contrast, the present invention employs mixed clathrates where the malodor is itself an entrapped guest moiety and while the present invention provides a multiplicity of examples of removing malodorous compounds, similar approaches are employed to remove other undesirable particulate or non-particulate environmental contaminants such as molds, spores, microorganisms, algae and the like.

The present invention thus provides a new approach to removing undesirable elements in the environment (that vary in molecular diversity, complexity, molecular weight, structure, size and shape from small molecules to macromolecules, in addition to constantly fluxing over time through decay) by spontaneously forming mixed host clathrates in the presence of the contaminants as guest moieties wherein these mixed clathrates form molecular and or supramolecular entrapments that form nanocages conformationally and antisymmetric to the guest moieties.

DISCLOSURE OF THE INVENTION

The compositions and methods of the invention are successful in removing undesirable contaminants from the environment. By providing specifically conformed nanocages, the compositions of the invention can adjust themselves to conform to the nature, diversity, and the flux over time of the potential guest moieties. Any organic entity, whether living or deceased, will transition from high complexity to the lowest malodorous chemical species possible. This flux in decay over time results in an ever evolving and changing set of malodors present in any given sample. The current invention exhibits the ability to adapt itself through continual rearrangement to the continuous change in size and diversity of the malodors present.

Thus, in one aspect, the invention is directed to a composition that spontaneously forms a supramolecular mixed host clathrate, comprised of unassembled nanoconstructs that in the presence of the moisture of the sample containing the malodor or through the ability of the malodor to hydrogen bond, spontaneously cross link to form a three dimensional bonded labyrinth that entraps desired guest moieties, which composition comprises at least first and second components that are different from each other, are hydrophilic and spontaneously self-assembling, and continuously rearranging, to form a dynamic asymmetric intercalated lattice and framework, wherein when contacted with potential guest moieties said composition forms nanocages that are conformationally mimetic and antisymmetric to said guest moieties present at any time.

It is also the basis of this invention that the bonding of malodor (guest moiety) to host be the same type of bonding used for anti-asymmetrical lattice mixed clathrate formation in situ. Furthermore, the type of bonding used should be compatible for both processes, working interchangeably, to achieve the same goal. Another basis of this invention is that the type of bonding utilized for both malodor bonding and for mixed clathrate formation be capable of stoichiometric rearrangement upon shear or decay to accommodate the introduction of new malodors in or to the sample. The type of bonding utilized is responsive to matter state transitions, i.e., solid to gas. Organic malodorous species bound are still allowed to decompose once the malodor has been contained and is set aside for disposal and final decomposition, wherein such bonding requires flexibility.

Generally, one component is a nanocomposite comprised of unassembled, high surface area reactive fumed silica nanoparticle subassemblies occurring in short branch chains and the other is a nanocomposite comprised of structurally unassembled aluminosilicate.

The nanocomposites of host components used as the basis for the formation of the latticed mixed clathrate are inorganic in structure yet sufficiently functionally reactive and suitable for use in an aqueous organic environment.

In addition to dynamically conforming the nanocages to the guest moieties, binding can be effected through hydrogen bonding, Van der Waals forces, or other types of bond provided by the host mixed clathrate.

In another aspect, the invention is directed to a method of removing undesirable materials from the environment by treating the environment in which they are contained with the invention compositions. The invention is also directed to the supramolecular mixed clathrates containing guest moieties that are formed upon treating the environment with the invention compositions

MODES OF CARRYING OUT THE INVENTION

This invention describes the nanocompositions and processes required for the in situ auto poetic formation of a supramolecular mixed clathrate complex for the express purpose of remediation with respect to undesirable environmental moieties that can be captured as guest moieties. A mixed clathrate is formed with an inclusion of a series of asymmetric guest moieties which are both entrapped in, and bonded to, mirror-imaged anti-asymmetric intercalated cages formed by a lattice comprised of two or more distinct host molecules.

The non-pre-reacted nanocomposite may be used as a dry powder admixture as the basis for formation of the mixed clathrate in situ. It is comprised of a combination of two or more distinct amorphous unassembled particulate or subparticulate nanostructures. The base compositions for the nanostructures serve as functionally reactive host molecules for the mixed clathrate.

The first and second host components may both be inorganic, but they differ in composition. Both host components are highly hydrophilic and spontaneously functionally reactive in situ as the means for the spontaneous formation of the mixed clathrate. Both host components of the nanocomposite are self-assembling. Functional group chemical reactivity of at least one of the host components may include hydrogen bonding as the basis for both lattice formation upon primary hydration in situ in order to form the mixed clathrate complex and also as the basis for hydrogen bonding of the guest moieties to the mixed clathrate lattice structure through the nanocage structures produced in the primary lattice. The guest moieties for the mixed clathrate may be anti-asymmetric malodorous compounds as found in a solid, liquid, or gaseous states, or combinations thereof, or may be larger entities such as mold, blood cells (for hemostasis), or the like The second host component is generally more electronegative than the first. Both host components in a dry powdered nanocomposite are self-assembling upon primary hydration forming an asymmetric polymorphous lattice that is both conformationally mimetic and anti-asymmetric to asymmetric guest moieties through the formation of nanocages. The mixed clathrate formed in situ constitutes an intercalated double lattice structure that is anti-asymmetric and polymorphous as well.

The supramolecular formed mixed clathrate complex is also self-rearranging upon shear, or the availability of new guest molecules which may appear over time as the result of decay. The term supramolecular is used to define a three-dimensional lattice, or labyrinth, that encompasses the totality of the sample to be treated and all the guest moieties thereof. The size of the lattice labyrinth can be anything from miniscule based on the sample to metric tons of waste and at any one time may include a diverse population of liquid, solid or gaseous materials varying in molecular weight. The size is only limited by the scope of the application and amount of nanocomposite material required.

Intercalation means the interaction of spontaneous self-assembling primary and secondary host molecules in the formation of a stable three-dimensional supramolecular lattice mixed clathrate labyrinth. The mechanism of mixed lattice interaction involves primary and secondary host components as co-constructing agents involved in a mixed composite integrated framework; alternatively the primary and secondary host components may serve as co-constructing agents for two distinct yet intercalated frameworks linked through open pores and cages; and or secondary host components may form distinct micro-frameworks and cage structures wherein the secondary clathrates are enclosed in the lattice framework of the lattice of the primary host component clathrate.

The supramolecular mixed clathrate complex captures, entraps and binds the many types of undesirable potential guest moieties that may be present in any given environment. The guest moieties are conformationally asymmetric in form, in that the guest moieties at any given time can be variable in size, chemical structure, molecular weight, chemical composition or functionality. To be chemically reactive with the mixed clathrate, the guest moieties may be inorganic, or organic and may include microorganisms or other cells. Preferably, they contain donors and/or acceptors for hydrogen bonding and or other functionalities for other types of bonding.

Dry powder admixtures of host components may be comprised of combinations of non-preformed host components admixed with preformed clathrates less than 5 microns in diameter. The non-preformed host component combinations and the preformed clathrates are typically both inorganic of different chemical composition. The non-preformed host components may be comprised of a mixture of bonding and non-bonding host components. All host components, whether non-preformed or preformed clathrates, would serve as the base composition for unassembled nano structures.

Hydrophilic hydrogen bonding host components preferably contain >8 functional reactive groups per square nanometer (capable of hydrogen-bonding), be nanoparticulate with an unassembled size of <30 nm, and have a surface area of >380 m$^2$/g. Nanostructure subassemblies would occur as three-dimensional branched short chain nanostructures cross-bonded through melt adhesion or hydrogen bonding. Hydrophilic non-hydrogen bonding host components would, by contrast, be polymorphous nanostructure subassemblies with an unassembled size of <600 nm, have unit pore sizes <25 Angstroms, and surface areas >700 m$^2$/g.

In one embodiment, a component of the invention compositions is an amorphous polymorphic composite of unassembled non-hydrogen bonding, synthetic zeolite, such as zeolite Y, or natural faujasite or mordenite non-crystalline framework subassemblies. Faujasite framework subassemblies, as preferred example would consist of truncated octahedral (beta cages or sodalite cages) connected through six member rings (6R), which upon crystallization would partially or fully form intercalated double-six rings (D6R, or hexagonal prisms) in tetrahedral arrangement within the framework of the primary host component lattice.

Nanoparticulate hydroxyl-derived fumed silica subassembly component that serves as a primary component of the potential mixed clathrate composition is nanoparticulate fumed silica which displays multiple hydrogen bond donors and acceptors.

The hydrogen bond donor/acceptor is capable of donating or accepting electrons or hydrogen from target malodor compounds with complementary hydrogen bond acceptors/donors in their structures, or from water containing target malodor compounds with or without complementary hydrogen bond acceptors/donors. Typical hydrogen bond donors of hydrogen are alcohols, amines, and to a lesser extent sulfhydryl. Acceptors include moieties with unshared electron pairs O, N, S and halide.

The reactive nanoparticulate fumed silica component that serves as a primary component of the potential mixed clathrate composition may itself associate with contaminant components through two complementary mechanisms. First, the polar surface of the nanoparticles interacts preferentially with polar compounds through hydrogen bonding with hydrogen bond donor and acceptor functionalities contained in the guest moiety to be sorbed into the composition. Second, because the nanoparticles in the compositions are themselves intricate matrices of silane-based chains, they can behave as clathrate hosts to absorb both polar and nonpolar guest moieties into the interior of the nanoparticles. Other forms of molecular attraction and binding may be involved.

However, the nanocomposite compositions of the invention further comprise a secondary component which is an aluminosilicate mineral—synthetic zeolite Y is particularly preferred. The aluminosilicate mineral is synthetic or natural, and is hydrophilic to allow for mixing with the reactive nanoparticulate fumed silica component. This solid phase carrier is not a hydrogen bond donor or acceptor. Under aqueous conditions, the solid phase carrier material is non-hydrogen bonding (to minimize dissolution) and self-assembling, such that it produces a polymorph of 100% crystallinity upon hydration. Upon interaction of the composition comprising the reactive nanoparticulate fumed silica and the solid phase carrier with water or target guest moieties or both, the two components of the nanocomposite interact to form a polymorphous, mixed clathrate complex.

The present invention encompasses any mixture of the two components, including: 1) the non-clathrate mixture of the two components, 2) a partial or single clathrate mixture, and 3) the mixed clathrate complex of the two components. More than two host molecules may be involved in mixed clathrate formation. The mixture would afford an excess amount of functionally reactive bonding groups relative to the amount of hydrogen donors on the guest molecules to be bound. The admixture may be powdered-base material, aerosolized, or in a liquid format. The admixture would maintain its chemical functionality with guest molecules upon drying (evaporation). The admixture may additionally encompass other odor control materials such as absorbents, adsorbents, neutralizers, masking agents or other conventional methods of odor control without adverse effect on mixed clathrate formation in situ.

The Primary (First) Host Component

The preferred primary hydrophilic host component in the functionally reactive nanocomposite is comprised of synthetic or natural functionally reactive amorphous hydroxyl-derived silica subparticulate nanostructure subassemblies, synthesized by vapor phase hydrolysis of silicon tetrachloride in a hydrogen oxygen flame at temperatures above 1800° C. Upon cooling silica dioxide molecules condense to form subparticulate nanostructures with diameters less than 30 nm (range 7-30 nm). Upon further condensation sub-particulate nanostructures attach and sinter together to produce small short chained subassemblies. Preferably, branch chain subassemblies have a length of less than 0.5 microns. Functionally reactive amorphous alkoxide-derived silica nanostructure subassemblies produced by this method are of the general formula $[SiO_x(OH)_{4-2x}]_n$. (This is not to be confused with non-reactive silica-based macro-composites such as silica gel or sized silica dioxide that have no functionality or structural basis for or applicability to the present invention.)

The functionally reactive fumed silica produced by this method is extremely light, non-dense, amorphous, hydrophilic, hydroscopic, and carries a net negative electrical charge and is difficult to handle under field conditions. The silica nanocomposite contains a high saturation of surface siloxane groups and silanol (hydroxyl) groups. Silanol groups occur as four populations depending upon moisture content and degree of substitution: isolated hydroxyl groups, hydrogen-bonded hydroxyl groups, vicinal hydroxyl groups (the vicinal pair), and the geminal variant containing two hydroxyls. Functionally reactive amorphous silica powders most suitable for use in nanocomposites for mixed lattice clathrate formation in situ are carefully equilibrated for normal surface moisture. The subassembly aggregation behavior of functionally reactive amorphous hydroxyl-derived silica powders was found to be dependent on the hydration force, which was modifiable by the surface silanol structure. The subassembly aggregation behavior is modifiable by the surface silanol structure. Subassemblies <30 nm in diameter are preferred, wherein the functionally reactive surface silanols are primarily isolated hydroxyl groups. Functionally reactive amorphous silica powders most suitable for use as primary host components have a moisture content of <1.5% and preferably <0.1% to reduce the number of hydrogen-bonded hydroxyl groups present. Functionally reactive silanol and siloxane groups produced to these specifications prove most useful for hydrogen bonding upon mixed clathrate formation. Functionally reactive silanols, thus formed and surface distributed produce a wide range of hydrogen bonded structures ranging from simple dimers, through various types of chain and sheets, to extended three-dimensional lattice networks when used for guest moieties sequestration and bonding. Further reinforcement of the mixed clathrate may incorporate appropriately derivatized functional graphene or fullerene nanostructures in sheet, tubular, or spherical form.

The overall electronegative charge, light nature and low density of the primary host component, although difficult to handle alone as a dry powder without a secondary host component, may itself function as a host for guest moieties if afforded the appropriate number and surface density of functionally reactive silanols for effective hydrogen bonding.

A prerequisite for both effective first host component lattice clathrate formation in situ and effective control is maintenance of a precise silanol-enriched "reactive state" for surface hydroxyls on the primary host molecule so as to assure maximal reactivity upon use. The saturation density (>8 functional reactive sites/nm$^2$), coupled with a small unassembled particulate nanostructure size (<30 nm) with high surface area (>380 m$^2$/g), a short branched chain subassembly length (<0.5 microns), and an overall net negative charge, are helpful to performance.

In preferred embodiments, the nanoparticulate reactive fumed silica comprises at least eight hydroxyl groups per square nanometer. Various levels of hydroxylated fumed silica are available commercially in grades of 150-400 with increasing levels of hydroxylation, varying upon moisture levels and extent of derivitization, varying in terms of reactive hydroxyls available per square nanometer.

As noted, the reactive nanoparticulate fumed silica has a high surface area. In some embodiments, the unassembled reactive nanoparticulate fumed silica has a surface area of at least 100, 150, 200, 250, 300, 350 m$^2$/g or more. In other embodiments, the surface area is at least 350 m$^2$/g. In still other embodiments, the surface area is about 380 m$^2$/g.

In some embodiments, the unassembled reactive fumed silica nanoparticles are less than 20, 30, 50, or 80 nm in diameter at 0.1% moisture. Size may be tested by a particle counter or SEM and moisture may be determined by weight before and after drying at 60° C. or higher. In other embodiments, the reactive fumed silica nanoparticles are less than 20 nm in diameter at 0.1% moisture. In other embodiments, the reactive fumed silica nanoparticles are less than 30 nm in diameter at 0.1% moisture. In some embodiments, the reactive fumed silica nanoparticles have a moisture content of <1.5%. In other embodiments, the reactive fumed silica nanoparticles have a moisture content of <0.1%. In some embodiments, the unassembled reactive fumed silica nanoparticles have a branched chain subassembly length of 1.0 micron or less, 0.75 microns or less, or 0.5 microns or less. In other embodiments, the unassembled reactive fumed silica nanoparticles have a branched chain subassembly length of 0.5 microns or less.

A commercially available example of reactive nanoparticulate fumed silica is available from Cabot of Boston, Mass., as Cab-O-Sil® EH5, or Elkem Materials EMS-211, Norway The availability of reactive hydroxyl groups at the surface and of oxygen associated with the silane portions of the silica provide opportunities for hydrogen bonding. As is understood, hydrogen bonding occurs by virtue of a hydrogen donor atom (which would be a hydrogen associated with a polar group such as N, O, or to a lesser extent S), with a hydrogen bond acceptor which is also a polar group, such as O, N, or to a lesser extent S. Thus, the oxygen groups of the siloxane can behave as hydrogen bond acceptors to hydrogens in guest moieties that are bound to electronegative atoms and the hydroxyl groups provide hydrogen donors to electronegative atoms in the guest moieties.

The Secondary (Second) Host Component

To maintain the maximum "functionally reactive state" for the primary host components in the nanocomposite it has been determined empirically that only certain inorganic chemical compounds and structures were structurally and functionally compatible in the nanocomposite as secondary host components that allow maintenance of that state.

The secondary host component in the nanocomposite is designed and selected to be both hydrophilic and electronegative. It was preferable to fabricate a material that had a lower (or higher as second choice) electronegativity than the silanol enriched functionally reactive, amorphous silica component so as to form a complexed nanocomposite that is still electronegative with an overall net negative Zeta potential. This condition allows for maintenance of a net negative charge for the blended nanocomposite complex and provides the necessary hydrophilicity. The admixture with secondary component makes the primary host component easier to handle by agglomerating and densing it without loss of functional group reactivity. In addition, the second host component is designed to minimize supramolecular disassociation and dissolution under high aqueous conditions, but must be self-assembling, in this case through amorphous crystallization upon hydration. The second host component also contributes to mixed clathrate formation and intercalates with the primary host component to produce a stable host mixed clathrate. Inherent to co-production of the mixed clathrate is required for enough flexibility to allow formation of anti-asymmetric mimetic macro-cages and nano-cages distributed throughout the lattice network around asymmetric guest moieties. Hydrophobic secondary host components are not useful as they do not mix with the primary hydrophilic host components and tend to form an interface layer on the surface of liquids which was not desired.

A large variety of naturally occurring and synthetic materials were screened to identify categories of materials useful as the second component. Examples of screened materials include natural clays, absorbent rocks, natural minerals, synthetic minerals, activated carbon, natural fibers, synthetic fibers, and the like. Only a certain class of synthetic minerals is compatible and affords properties such as spontaneous self-assembly, adhesion to substrata, among others, conducive to mixed clathrate formation in situ to aid in mixed clathrate stabilization.

Unassembled non-crystalline amorphous synthetic or natural faujasite and mordenite nanostructure subassemblies exhibit spontaneous polymorphous crystallization properties and appropriate adherence to substrata in an aqueous environment that are compatible when used as part of a nanocomposite to aid in production of a mixed lattice clathrate. Non-reactive amorphous faujasite and mordenite nanostructure subassemblies are custom synthesizable or natural crystalline aluminosilicates that can be readily produced in dry powdered form. The presence of alumina in the framework of the composite results in a net negative framework charge which is ideal, and the sub-particulate nanostructures are electronegative relative to the primary host component. Other crystalline silicates such as zirconium silicate, and the like may be used.

Dry-gel hydrothermal process was used for synthesis of amorphous faujasite as described in U.S. Pat. No. 3,130,007 and U.S. Pat. No. 3,594,121 with modifications to produce custom host subassemblies. For example, non-reactive colloidal silica was mixed with a solution of sodium hydroxide and sodium aluminate at ambient temperature, followed by digestion for twenty-four hours. The reaction mixture is heated to 200° Fahrenheit for an additional forty-eight hours to effect initial nanostructure subassembly formation. Metallic aluminosilicate sub-particulate nanostructure subassemblies with a $SiO_2/AlO_3$ ratio of 3-6 were obtained with a size of <600 nm, had unit pore sizes <25 Angstroms, and surface areas >700 $m^2/g$. The sodium cationic form was utilized to afford highest attraction for hydration water. Although the 25 Angstrom pore allowed the synthesized material to bind ammonia upon cation exchange as nominal cation, this feature was only secondary to its use for mixed clathrate formation and stabilization.

The synthesized non-reactive amorphous faujasite nanocomposites produced under the above conditions yielded nanostructure subassemblies <600 nm in size. Nanostructure subassemblies were polymorphous and asymmetric in shape and consisted of truncated octahedral (beta cages or sodalite cages) connected through six member rings (6R), which upon crystallization would form double-six rings (D6R, or hexagonal prisms) in a tetrahedral arrangement.

Synthesis of non-reactive amorphous mordenite nanostructures was performed using a modification of the procedure described in U.S. Pat. No. 3,531,243. Metallic aluminosilicate subparticulate nanostructure subassemblies with a $SiO_2/AlO_3$ ratio of 45-55 were obtained with an unassembled size of <600 nm with surface areas of >425 $m^2/g$. The framework of mordenite also contained a net negative charge and exhibited spontaneous self-assembly with and amorphous crystallization upon primary hydration in combination with functionally reactive primary component. Synthetic mordenite has a relatively large pore structure containing two types of pores, one straight, and one elliptical. Synthetic mordenite exhibits excellent substrata adhesion properties to organic matter or other structures upon primary hydration, which is advantageous. The substrata adhesion aids in the attachment of the nanocomposites to hydrated solid matter such as fecal material.

The addition of non-reactive amorphous synthetic or natural faujasite and or mordenite nanostructures also aids in the stabilization of the first host molecule clathrate labyrinth formed through structural co-stabilization. Other host molecules may also contribute to the formation and stabilization of mixed clathrates in situ. As example, in artificial blood clot formation and hemostasis, naturally occurring fibrinogen and fibrin would aid in mixed clathrate formation.

In summary, the secondary components for the nanocomposite compositions are hydrophilic, inorganic minerals, such as microporous aluminum silicate minerals or other volcanic silaceous materials. Particular examples include molecular sieves, bentonites such as aluminum phyllosilicate, montmorrilite clay, or sodium bentonite, or zeolites such as faujasite, mordenite, analcime, chabazite, clinoptilolite, heulandite, natrolite, phillipsite, or stilbite. Exemplary commercially available materials are the bentonite Tex. Sodium Bentonite, available from Texas Sodium Bentonite, Inc., of Comanche, Tex., and the zeolites ZK406H® and St. Cloud Natural Zeolite, which is a natural clinoptilolite form of potassium aluminosilicate, available as powders and granules from a number of sources including GSA Resources, a subsidiary of St. Cloud Mining Company of Winston, N.M. Zeolite Y is particularly preferred. These solid alternate phase carriers are commercially available in various particle sizes. These secondary components may also have additional properties, for example, zeolite ZK406H binds ammonium, and bentonite absorbs water. Zeolite Y as faujasite occurs naturally, but the synthetic form is preferred.

The Nanocomposites

To prepare compositions of the invention comprising reactive fumed silica nanoparticulates and a solid phase carrier, it is generally only necessary to form an intimate admixture of the components. The components may be added in any order, although it is preferable to mix the highly hydroxylated nanoparticulate fumed silica such as Cab-O-Sil® EH5 with a solid phase carrier as a separate process, which mixture can then readily be handled, and then supplied to any additional components.

Dry powdered amorphous synthetic faujasite nanostructure subassemblies, once hydrated, produce a slurry with an alkaline pH of 11-12 that exhibits poor spontaneous crystallization, when used alone, but an improved polymorph crystalline structure is obtained for mixed clathrate formation when a nanocomposite of functionally reactive primary component subassemblies were mixed with this secondary component. The low pH of approximately 2-4 for functionally reactive amorphous fumed silica in slurry resulted in a final pH for the admixture of 7-8 resulting in improved polymorph crystalline structure formation in Table 1. Since most biological malodorous species are formed at a pH of 5-8, this added further buffering by the sample at the preferred pH.

TABLE 1

|  | pH of Slurry | Initial Crystallinity | Ending Crystallinity |
| --- | --- | --- | --- |
| Faujasite alone | >11 | 3% | 24% |
| Mixture | 7 | 16% | 99% |

The utilization of a nanocomposite comprised of functionally reactive amorphous silica nanostructure subassemblies in combination with unassembled synthetic Zeolite Y, or faujasite, or mordenite nanostructure subassemblies results in a stable dry, often powder, admixture for supramolecular mixed lattice clathrate formation for guest moiety elimination suitable for field applications. The nanocomposites prepared as described above result in transient polymorphs as dry powder agglomerates of electrostatically bonded functionally reactive amorphous silica and cationic aluminosilicate such as faujasite. Nanocomposites prepared as such showed a high hydrophilicity due to the overall negative Zeta potential of the complex, and the high functional reactivity of the silanol groups on the primary host component were well maintained. The nanocomposites show high affinity for water further enhanced by the cationic faujasite.

The nanocomposites described above may contain additional components, including, for example, additional malodor control materials or other materials that effect ease of handling, dust control, or moisture control. Additional components include, for example, additional solid phase carriers, moisture control agents, heavy metal adsorbents, nitrogen adsorbents, heavy metal scavengers, or other malodor control materials.

Further additional components can, for example, include: bulk fillers and carriers; flocculation aids; biocides or biostats; materials that serve as a web, weave, fabric, fiber, polymer, sack, sachet, drape, or the like; additional nanomaterials such as functionalized graphenes or fullerenes, or the like, humectants; insect and or animal repellents; controlled release agents, bulking agents, densing agents, light-weighting agents, and the like; soil amendments, or fertilizers; surfactants, gelling agents, stabilizers, foaming agents, clumping agents, non-stick releasing agents, anti-stats, or the like; detergents, solubilizers, enzymes; oxidizing agents (e.g., bleach or ozone), reducing agents, chelating agents, coupling agents, cross-linking agents, scavengers, and the like; absorbents, adsorbents, activated carbon, silica gel, powdered cellulose, charcoal, purified siliceous earth, zeolites, nitrogen sorbents, carbon dioxide sorbents (e.g., barium hydroxide lime, soda lime), or the like; acids, bases, metals and metal complexes, solvents, diluents, salts, odor re-characterizing agents, or the like; temperature indicators, moisture indicators, marking dyes or chemicals, tracers, indicator dyes or media; thickening agents, solidifying agents, endothermal or exothermal agents; fermentation agents; desiccating agents, swelling agents, pyrogenic agents, filtering aids, or the like, bleaching agents; agents for body hygiene; medicines; antimicrobial agents; decorative dyes or colors, or perfumes; or combinations thereof.

Examples of suitable moisture control and/or clumping additives include silica gel, sodium polyacrylate. Others include starch-based absorbents, such as those with grafted side chains of calcium or potassium salts of (2-propenamide)$_n$-co-2-propenoic acid copolymers. Commercially available starch derivatives of this type are available, for example, from Absorbent Technologies, Inc., of Beaverton, Oreg., under the trade name REON™. A particularly useful example is REON™200 granules.

Suitable heavy metal scavengers include cationic ion exchangers, such as those with specificity for lead, arsenic, mercury, or other heavy metals, and those that function even in the presence of competing ions such as calcium and magnesium. The heavy metals are trapped in the ceramic matrix, whereas the smaller metal ions responsible for hardness of water are not. Suitable material abbreviated "ATS" are available from BASF. The portion of the compositions that comprise cationic trapping agents such as ATS will vary with the nature of the target but are typically in the range of 0.01-4% by weight, preferably 0.5-1.5% by weight.

Various carriers and bulk fillers may be used as additives and are hereby included by reference. These include but are not limited to; clumping and non-clumping clay minerals; synthetic and non-synthetic absorbents or adsorbents; absorbent rocks; natural minerals such as gypsum and bassenite; synthetic minerals; natural minerals or composites; synthetic fibers; and combinations thereof.

Other control agents such as adsorbents, absorbents, neutralizers, masking agents, or other conventional methods of odor control without adverse effect on mixed clathrate formation in situ. For example, bulk absorbents may serve to remove water hence increasing lattice formation. Adsorbents may also serve to temporarily sequester or remove specific chemical species through absorption wherein the mixed clathrate will hydrogen bond the odoriferous materials upon eventual release from the absorbent.

Methods of Use

The mixed clathrate form of the nanocomposite that forms upon interaction with guest moieties result in binding compression and adhesion of guest moieties are dynamic materials. Mixing the reactive nanoparticulate fumed silica and the secondary aluminum silicate component creates a supramolecular mixed clathrate complex through spontaneous self-assembly of the two components into a stable, three-dimensional lattice.

One major category of guest moieties is malodorous compounds. Malodor causing chemicals that are targets for remediation, as described earlier, include both high and low molecular weight organic malodors, varying in molecular diversity and complexity from the whole organism to the smallest molecular species based on the active dynamic process of entropic decay.

The nanocomposites described herein may be used in dry, wet solid, wet liquid, or gaseous matter odor control applications. Exemplary solid matter odor control applications include but are not limited to: treatment of domestic trash containers, domestic diaper pails, retail business trash containers; industrial trash handling (trash bins, drop-offs, refuse trucks); treatment of boots and shoes (e.g., for hunters, fishermen, golfers, bowlers, athletes, diabetics); treatment of foot odor; automobile fresheners; treatment of recreational vehicles; treatment of school and gym lockers, treatment of refrigerators and freezers; landfill treatments; cat litter formulations; pet cages, bedding and pet areas; treatment of carpeting or fabrics; treatment of consumer-based composting; sanitary napkin treatments; large animal bedding/stalls (e.g., dairy, horse, zoo); treatment of manure (e.g., hog, cow, horse, chicken, turkey); treatment of fish processing plants and renderings; treatment of avian bedding (chicken, turkey); treatment of chicken/turkey/dairy farm exhaust fumes; treatment of crematorium exhausts; treatment of brewery exhaust fumes; treatment of slaughter houses and animal renderings; and commercial waste processing with potential fertilizer preparation. Exemplary liquid matter odor control applications include but are not limited to: treatment of rural septic tanks, waste water run-off from farms; open cesspool treatment as widely used in Asia; waste-water lagoon treatment; treatment of human sewage; and treatment of wood and pulp mills Exemplary gaseous matter odor control applications include, for example, control of gaseous malodor compounds from rural waste-water lagoons and Kraft pulp mills.

The composition of the invention may also be used in wound dressings, household disinfectants, toilet applications, room deodorizers, coal plant scrubber, mouthwash/oral rinse, sink/disposal cleaners, cooking waste, and body wash (e.g., for humans or pets for skunk odor removal).

In addition to removal of malodorous compounds, the invention compositions are useful for removal of a variety of undesirable contaminants in an environment, including mold, bacteria or other microorganisms, algae, spores, and the like, that is any contaminant that can serve as a guest moiety in the host mixed clathrate.

The compositions may be used in any suitable formulation. Delivery mechanisms may be single composite or multi-step, multi-composite processes. For example, nanocomposites may be delivered in solid form as granules or powders, or formulated as liquids, sprays, aerosols, suspensions, emulsions, washes, oils, and the like, or formed into three-dimensional devices or structural frameworks, such as tubes, boxes, cylinders, filters, and the like. Compositions may be applied using any suitable application device, such as pouches, sachets, drapes, blankets, dispensed powders or aqueous or nonaqueous liquids, and the like; propellant aerosols; pellets; integrated into or onto webs, fabrics, filters, containers, or the like; integrated into dissolvable structures such as capsules, or other release containers; integrated into containers comprised of plastic, glass, metal, fiber, fabric or the like; by heat, flame, or mechanical or electrical assisted dispersion devices, or the like; and combinations thereof. Application may also be accomplished by use of filters, dispensing agents, fans, or other processes suitable for the particular application. In some embodiments, compositions are prepared off-site before malodor treatment and in other embodiments, compositions are prepared onsite. In some embodiments, treatment methods include recapture and compounding of by-products, as in fertilizer, control of odors streams, or custom processes.

The composition may be applied in a thin layer to the area to be treated. For application to liquid environments, it is not necessary to agitate the mixture once the composition is applied, but this is often beneficial, and can be accomplished by using wave actions, pool mixers or air jets below the surface of the liquid. For larger treatments, compositions may be deployed with an airstream, tuning the rate of delivery so as to prevent any static buildup. If equipment is used to deliver the composition, therefore, it should be grounded. For remediation of decomposed animal, plant, or other waste material, similar application to assure physical contact with the decomposed material is required.

The following examples are offered to illustrate but not to limit the invention.

Example 1

Preparation of Reactive Nanoparticulate Fumed Silica

Forty grams of silicon tetrachloride are hydrolyzed in a hydrogen oxygen flame at a temperature above 1800° C. Upon cooling, silica dioxide molecules condense to form sub-particulate nanostructures with diameters less than 30 nm (range 7-30 nm). Upon further condensation, sub-particulate nanostructure attach and sinter together to produce small short-chained assemblies of 0.5 microns or less in length. The resulting subassemblies are of the general formula $[SiO_x(OH)_{4-2x}]_n$.

Example 2

Preparation of Amorphous Synthetic Faujasite

Amorphous synthetic faujasite was prepared using a dry-gel hydrothermal process as described in U.S. Pat. Nos. 3,130,007 and 3,594,121, with modifications to produce custom subassemblies. For example, non-reactive colloidal silica was mixed with a solution of sodium hydroxide and sodium aluminate at ambient temperature, followed by digestion for 24 hours. The reaction mixture was heated to 200° F. for an additional 48 hours to effect initial nanostructure subassembly formation. Metallic aluminosilicate sub-particulate nanostructure subassemblies with a $SiO_2/AlO_3$ ratio of 3-6 were obtained with a size of <600 nm, unit pore sizes <25 Angstroms, and surface areas >700 $m^2/g$. Nanostructure subassemblies were polymorphous and asymmetric in shape and consisted of truncated octahedral (beta cages or sodalite cages) connected through six member rings (6R), which upon crystallization would form double-six rings (D6R, or hexagonal prisms) in a tetrahedral arrangement.

Example 3

Preparation of Amorphous Synthetic Mordenite

The hydrothermal process described in Example 2 was also utilized for synthesis of non-reactive amorphous synthetic mordenite nanostructures using a modification of the procedure described in U.S. Pat. No. 3,531,243. Metallic aluminosilicate sub-particulate nanostructure subassemblies with a $SiO_2/AlO_3$ ratio of 45-55 were obtained with an unassembled size of <600 nm with surface areas of >425 $m^2/g$. The framework of mordenite also contained a net negative charge and exhibited amorphous crystallization upon hydration. When combined with fumed silica nanoparticles the combination exhibited spontaneous self-assembly into mixed clathrates. Synthetic mordenite is a relatively large pore structure containing two types of pores, one straight, and one elliptical. Synthetic mordenite was also noted to exhibit excellent adhesion properties to organic matter upon initial hydration and was selected primarily for this property. This adhesion further aided in the attachment of the nanocomposites to hydrated solid matter such as fecal material.

Example 4

Preparation of Blended Nanocomposite Compositions

A nanocomposite comprised of reactive fumed silica nanoparticles in combination with unassembled synthetic faujasite or synthetic mordenite nanostructure subassemblies resulted in a stable dry powder admixture useful for malodorous compound elimination in field applications. The nanocomposites of the silica of Example 1 and the secondary component of Example 2 or 3 result in the production of transient polymorphs as dry powder agglomerates of electrostatically bonded functionally reactive amorphous silica and cationic synthetic faujasite. Nanocomposites prepared as such showed a high hydrophilicity due to the overall negative Zeta potential of the complex, and the high functional reactivity of the silanol groups on the fumed silica nanoparticles were well maintained. The nanocomposites showed high affinity for water further enhanced by the cationic synthetic faujasite.

Example 5

Composition for Kleen N Purr Odor Eliminator

Six grams of Cab-O-Sil™ EH5 are added to 893 g of Texas Sodium Bentonite and mixed intimately. This mixture is then added to 100 g of ZK406H. One gram of synthetic zeolite Y is also added. The final mixture is packaged for use.

Example 6

Composition for Kleen N Pun Enhanced Absorbance

Six grams of Cab-O-Sil™ EH5 are added to 892 g of Texas Sodium Bentonite and mixed intimately. This mixture is then added to 100 g of ZK406H® and 2 g of sodium polyacrylic acid. The final mixture is packaged for use.

Example 7

Composition for Kleen N Pun Enhanced Clumping

Six grams of Cab-O-Sil™ EH5 are added to 881 g of Texas Sodium Bentonite and mixed intimately. This mixture is then added to 100 g of ZK406H®, 12 g of REON™ 200, 1 g of sodium polyacrylic acid. The final mixture is packaged for use.

Example 8

Composition for Kleen N Pun Booster

Two grams of Cab-O-Sil™ EH5 are added to 897 g of ZK406H®, and 1 g of synthetic zeolite Y and mixed intimately. This mixture is then added to 1 g of REON™ 200 and 100 g of silica gel. The final mixture is packaged for use.

Example 9

Composition for Kleen N Pun Carpet and Pet Area Deodorizer

Two grams of Cab-O-Sil™ EH5 are added to 847.5 g of ZK406H®, and 1 g of synthetic zeolite Y and mixed intimately. This mixture is then added to 0.5 g of REON™ 200, 49 g of silica gel, and 100 g of St. Cloud Natural Zeolite. The final mixture is packaged for use.

Example 10

Composition for Avian Odor and Foot Odor

One gram of Cab-O-Sil™ EH5 are added to 998 g of ZK406H®, and 1 g of synthetic zeolite Y and mixed intimately. The final mixture is packaged for use.

Example 11

Composition for Dri-Remediation Granules

One gram of Cab-O-Sil™ EH5 are added to 972 g of Texas Sodium Bentonite, and 1 g of synthetic zeolite Y and mixed intimately. This mixture is then added to 13 g of macroporous nonreactive silica gel and 13 g of St. Cloud Natural Zeolite. The final mixture is packaged for use.

Example 12

Composition for Dri-Remediation Carpet Powder

Two grams of Cab-O-Sil™ EH5 are added to 8475 g of ZK406H®, and 1 g of synthetic zeolite Y and mixed intimately. This mixture is then added to 0.5 g of REON™ 200, 50 g of nonreactive macroporous silica gel, and 100 g of St. Cloud Natural Zeolite. The final mixture is packaged for use.

Malodor Remediation Test Examples

Test Example 1—Ammonia

Nanocomposite silica compositions were prepared as described above in Example 1. The dry powdered preparations were enriched for surface silanols and contained <0.1% hydration moisture. Preparations were evaluated for clathrate formation and malodor efficiency. To 0.5 g of dry powder nanocomposite in a 15 mL closed container was added 150 mL of ammonia solution (28.8 wt. % $NH_3$ in water at 15.5° C.; 34.8% $NH_3$). Olfactory readings were taken at 1 and 5 minutes by two independent blind operators and scored on a 1-10 scale, or were read using a Minimax-XP-$NH_3$ Ammonia ($NH_3$) Gas Detector for low levels. Results are shown in Table 2.

TABLE 2

Ammonia Binding Capacity of Nanocomposites

| Preparation | Surface Area ($m^2/g$) | Diameter (nm) | Mean Malodor Level (1-10 Scale) |
| --- | --- | --- | --- |
| None | NA | NA | 10 |
| 1 | 130 | >80 | 2.5 |
| 2a | 150 | >80 | 2.5 |
| 2b | 150 | >80 | 2.5 |
| 3 | 170 | >80 | 2.5 |
| 4a | 200 | >50 | 3.5 |
| 4b | 200 | >30 | 2 |
| 4c | 200 | >30 | 2.5 |
| 5 | 325 | <30 | 2 |
| 6a | >380 | <20 | 0.5 |
| 6b | >380 | <20 | 0 |
| 6c | >400 | <20 | 0 |
| 6d | >375 | <20 | 0 |

All tested preparations formed crystalline clathrates in situ and bound ammonia. The most effective preparations had a surface area of greater than 380 $m^2/g$, with a sub-particulate nanostructure diameter less than 20 nm, and a subassembly size of less than 0.5 microns at <0.1% moisture. Once the clathrate was formed, ammonia gas was not detectable upon opening closed containers for up to two additional months of testing.

Test Example 2—Sulfur Malodor Compounds

Nanocomposites prepared as in Example 1 were evaluated for $R_2$—S group malodor binding. As a source of 3-(methylthio)propionaldehyde, 150 mL of undiluted fresh white onion extract was added to 0.5 g of dry powder nanocomposite in a 15 mL closed container. Blind olfactory readings were taken after 5 minutes by two operators and scored on a 1-10 scale. Results are shown in Table 3.

TABLE 3

Methional Binding Capacity of Nanocomposites

| Preparation | Surface Area ($m^2/g$) | Diameter (nm) | Mean Malodor Level (1-10 Scale) |
| --- | --- | --- | --- |
| 1 | 150 | >80 | 5.5 |
| 2 | 170 | >80 | 5 |
| 3a | 200 | >50 | 4.5 |
| 3b | 200 | >50 | 5.5 |
| 3c | 200 | >30 | 4.5 |
| 4 | 325 | <30 | 4.5 |
| 5 | >380 | <20 | 1 |
| 6 | None | None | 10 |

Results showed that the malodors produced by sulfur-containing compounds in organic extracts were effectively removed by nanostructure composites. Materials remained effective at a two-week test timepoint. Comparable results were obtained with allicin (2-propene-1-sulfinothioic acid S-2-propenyl ester) using fresh extracts of garlic.

Test Example 3—Ammonia and p-Chlorobenzene Malodor Compounds

Nanocomposites prepared as in Example 1 were evaluated for binding of excess liquid ammonia and excessive amounts of solid para-chlorobenzene malodor binding. To four separate 0.5 $ft^2$ closed containers, either 100 mL of concentrated ammonia hydroxide or 500 g of solid para-chlorobenzene crystals were added to two each of the containers. Olfactory readings were taken blind by two operators of samples with and without nanocomposite treatment at various timepoints (t=zero, 24 hours, 48 hours, and 6 days) and scored on a 1-10 malodor scale. Results are shown in Table 4.

TABLE 4

Ammonium Hydroxide and p-Chlorobenzene Binding Capacity of Nanocomposites

| Malodor | Nanocomposite Treatment | Mean Malodor Level | | | |
|---|---|---|---|---|---|
| | | t = 0 | t = 24 h | t = 48 h | t = 6 d |
| Ammonium Hydroxide | No | >10 | >10 | >10 | >10 |
| | Yes | >10 | 2 | 1 | 0.5 |
| p-Chlorobenzene | No | 7 | 5 | 6 | 6 |
| | Yes | 7 | 3 | 2 | 2 |

Addition of nanocomposites to excess ammonium hydroxide liquid or excess solid p-chlorobenzene proved effective at malodor removal in closed systems for up to 6 days. The addition of nanocomposite to ammonium hydroxide resulted in the immediate formation of a wet to the touch cake which the operators were able to pick up and smell directly. The cake could also be broken and was not brittle, and further olfactory readings indicated little if any residual ammonia smell. The wet cakes devoid of malodor were visual evidence of supramolecular lattice mixed clathrate formation which rendered the sample malodorous in a ~65% aqueous environment. The absence of ammonia odor was not due to escape from the container as the untreated control exhibited strong malodor throughout the study. Depending upon the application it is beneficial to add a second lattice forming host component to the nanocomposite (containing the primary host component) to produce a structurally more reinforced mixed clathrate.

Test Example 4—Amine Malodor Compounds

Nanocomposites prepared as in Example 1 were evaluated for amine binding under conditions of continuous putrefaction. As a source for both solid and gaseous trimethylamine, putrescine, and cadaverine, three 500 g portions of fresh catfish were allowed to sit at room temperature for 24 hours prior to use in the study. Each of the 500 g portions were placed in a 1.0 ft$^3$ closed container. One portion was evenly coated with 5.0 g of nanocomposite and placed back in the container, a second portion was placed on one side of the container fitted with a short partition and 5.0 g of nanocomposite was placed in the container adjacent to the sample but not in direct contact; and the third portion served as control receiving no treatment. All three portions were held outdoors at room temperature for up to ten days. Ambient temperatures ranged from 85-92° F. during the day to 70-74° F. at night. Olfactory readings were taken blind by two independent operators and scored on a 1-10 scale. A mean malodor level of 2 is odor that is slightly noticeable but tolerable; a value of less than 1 was assigned when the odor was barely discernible. Results are shown in Table 5.

TABLE 5

Amine Binding Capacity of Nanocomposites

| Nanocomposite Addition | Mean Malodor Level | | | | |
|---|---|---|---|---|---|
| | t = 0 | t = 2 days | t = 4 days | t = 6 days | t = 10 days |
| None | 10 | 9 | >10 | >>>10 | >>>10 |
| Direct Contact | 10 | 2** | 0.5 | 0.5 | 0.5 |
| Indirect Contact | 10 | 5 | 1 | 1 | 1 |

The control condition of no treatment exhibited advanced decomposition within 2 days and got progressively worse. Although the olfactory scale was topped at 10, the malodor produced was well above this and putrefaction was evident up to 500 yards away upon opening the container. There was also evidence of heat production, visible dehydration, and vapor release from the material. In contrast, the coated material exhibited a slightly noticeable odor at 48 hours that was barely perceptible after that. The material was encrusted in a lattice labyrinth and exhibited little evidence of decay. On day 10 the material was picked up and no odor was sensed. The material was cut in half and had the same appearance and smell on the cross cut as prior to treatment but appeared dry. The material was held another 20 days under ambient conditions and no evidence of decay was noted. The test material that had nanocomposite placed next to it in the container exhibited some minor signs of decay at 48 hours that was minimal in contrast to the untreated sample, malodor was minimal after that timepoint. At day 10 the material had a fatigued look but was dry and intact.

Test Example 5—Digestion By-Products

Nanocomposites of Example 1 were evaluated for malodor control of by-products of digestion. Nanocomposites consisted of varying levels of reactive fumed silica nanoparticles prepared as in Example 1 and varying levels of uniform spherical preformed ceramic nano-caged clathrates of 0.1-0.3 micron diameter as secondary host components, synthetic zeolite Y, ranging in weight percents of 100:0 to 0:100 preformed spherical secondary clathrates were ceramic in composition and contained <25 Angstrom pores containing a sodium cation. Secondary clathrate material was used as the means to absorb additional moisture from the sample, were structurally inert, and did not intercalate directly with the framework of the lattice produced by the primary host component but upon examination was found embedded throughout the lattice.

As a source for both solid and gaseous forms of skatole (3-methyl-1H-indole), volatile fatty acids (acetic acid, propionic acid, butyric acid, isobutyric acid, valeric acid, 2-ethyl butyrate), and putrescine, 20 g aliquots of fresh human (and or porcine) feces were placed into 3 inch diameter flat bottom 50 mL sealed containers. For the study, each container containing the sample was opened and equal amounts of nanocomposite were added to just cover the fecal material (~0.5 g). Olfactory readings were taken blind by two independent operators over 5 days and scored on a scale of 1-10. Results are shown in Table 6.

TABLE 6

Digestion By-Product Malodor Control

| Nanocomposite Ratio (Primary/Secondary) | Mean Malodor Level | | |
|---|---|---|---|
| | t = 0 | t = 1 day | t = 5 days |
| None | 10 | 10 | 10 |
| 100/0 | 10 | 3 | 2 |
| 75/25 | 10 | 1 | 3 |
| 50/50 | 10 | 1 | 3 |
| 25/75 | 10 | 3 | 3 |
| 0/100 | 10 | 9 | 8 |

A reduction in digestion by-product malodor was observed within 24 hours for all conditions except for the sample without any reactive fumed silica (0/100). The secondary component (faujasite) may have a pore size too small to entrap larger malodorous organic molecules, and without the reactive fumed silica, no supramolecular lattice clathrate would be formed to entrap the guest moieties. The reactive fumed silica nanoparticulate material was required for effective malodor control and for formation of a mixed lattice clathrate.

For the other samples tested, the presence of the solid phase carrier did not inhibit formation of mixed clathrates by the reactive fumed silica nanoparticles and the carrier helped in moisture control. After 48 hours, however (data not shown), the nanocomposite covering the feces began to crack at higher levels of secondary component 0/100, 25/75 owing to the presence of an excess of the secondary preformed clathrates in the lattice framework of the mixed clathrate formed by the reactive silica nanoparticles. The preformed clathrates (faujasite) interfered with mixed lattice clathrate structural integrity over time especially at higher concentrations (0/100, 25/75) and this resulted in over drying. As a result, for 0/100 malodors on day 5 were elevated relative to day 1 but were still much less than the untreated control. A structurally compatible and supportive secondary lattice-forming host component was evident to enhance the structural integrity of the labyrinth over time to avoid cracks and fissures, provided it is not used as the major component.

Test Example 6—Digestion By-Product Malodor Control with a 90/10 Nanocomposite Primary nanocomposites were constructed using a 90/10 weight ratio of fumed silica nanoparticles (EH5) admixed with amorphous synthetic faujasite nanostructure subassemblies with a size less than 600 nm, unit pore sizes of less than 25 Angstroms, and a surface area of greater than 700 m$^2$/g. Formation and stabilization of the primary nanocomposite generated the Initial Blend composition, and a second composition was prepared by admixing the Initial Blend at an 8.2/91.8 ratio with various bulking agents, including natural chabazite, natural clinoptilolite, and preformed ceramic clathrate, to generate and Initial Blend with Filler.

The resulting preparations were tested for malodor control over time of freshly collected well-soiled diapers containing fecal material in a closed environment. Three test conditions were studied: no nanocomposite treatment; direct treatment (coating) of fecal material; and proximal exposure. Test materials were placed into 0.5 ft$^3$ sealed containers and incubated at room temperature for 6 days. Olfactory readings were made blind by two independent operators and scored on a 1-10 scale. Results are shown in Table 7.

TABLE 7

Digestion By-Product Malodor Control with 90/10 Nanocomposite

| Nanocomposites Tested | Nanocomposite Condition | Mean Malodor Level (1-10) | | |
|---|---|---|---|---|
| | | Zero | 2 Days | 6 Days |
| Initial Blend | None | 10 | 8 | 10 |
| | Direct Contact | 10 | 0 | 0 |
| | Indirect Contact | 10 | 2 | 0.5 |
| Initial Blend with Filler | None | 10 | 10 | 10 |
| | Direct Contact | 10 | 1 | 0 |
| | Indirect Contact | 10 | 1 | 0 |

The filler is ZK406H natural chabazite.

Relative to the composition tested in Example 5, this composition demonstrated improved digestion by-product malodor control at the 48 hour timepoint, and up to day 6. No cracking of the supramolecular labyrinth covering the fecal material was evident, and no recurrence of malodor occurred after 2 days up to day 6. Effective malodor control was observed both with the initial nanocomposite blend of reactive fumed silica nanoparticles and secondary component, and with the initial blend further admixed with various bulk fillers. Compositions with bulk fillers were also effective at controlling gaseous malodor control at 2 and 6 days. Both direct and indirect contact with the fecal material, as one would encounter in the application in a diaper pail, were effective.

Test Example 7—Malodor and Mold Remediation for Soiled Carpet

The blended nanocomposite with fillers of Example 6 was evaluated for efficacy in removal of gaseous ammonia from soiled carpet and for inhibition of mold growth in wet carpet upon storage. To evaluate removal of ammonia from carpets, fixed areas of carpet were placed in a closed system outfitted with a conical lid that was adjoined to an analytical ammonia gas meter. Meter readings were taken after ammonia addition for both untreated and post-treated carpet samples. Ammonia carpet levels prior to treatment served as baseline. Results are shown in Table 8.

TABLE 8

Malodor Removal Efficacy for Soiled Carpet

| Run | Nanocomposite Application | Ammonia (ppm) | | |
|---|---|---|---|---|
| | | Pre-Treatment | 5 min | 15 min |
| 1 | Untreated | 190 | 94 | 69 |
| | Treated | 190 | 16 | 0.5 |
| 2 | Untreated | 140 | 69 | 55 |
| | Treated | 140 | 21 | 0 |

Results demonstrated an 85-92% reduction in ammonia gas at 5 minutes post-application and a 99.7-100% reduction after 15 minutes post application.

To assess inhibition of mold growth over time, fixed areas of used carpet were saturated with water and either treated or not treated with the nanocomposite blend of Example 6 (Initial Blend without Filler). Test samples were placed in moisture proof sealed bags to prevent moisture loss and incubated in the dark at room temperature for up to 15 days after which they were dried. Olfactory readings were taken over time for the presence of mildew and scored on a 1-10 scale. Readings at time zero, 5 days, and 10 days were wet readings; readings at 15 days were dry readings. Results are shown in Table 9.

TABLE 9

Effect of Nanocomposite on Mold Growth Under Damp Conditions

| Nanocomposite Treatment | Mean Malodor Level | | | |
|---|---|---|---|---|
| | Zero | 5 Days | 10 Days | 15 Days* |
| Yes | 0 | 0 | 0 | 0 |
| No | 0 | 3.0 | 8.0 | 8.0 |

*dry reading, all prior readings were wet.

Results demonstrate that test nanocomposites are effective at retardation of mold growth over time evidenced by inhibition of mold malodors.

Test Example 8—Nanocomposite as Cat Litter Additive

A cat litter nanocomposite as described in Example 7 was evaluated for efficacy in ammonia reduction compared to six of the leading national brands of cat litter. Fixed identical quantities of each cat litter were added to a 50 mL closed container outfitted with an analytical ammonia gas meter at the top. Concentrated ammonium hydroxide equivalent to 5× the average ammonia output for a cat from urea over 24 hours was added (about 250 ppm). Meter readings were taken at regular intervals after ammonia addition. All ammonia gas that was emitted was detected by the meter at the top of the container over time. Comparative results with commercial products are shown for composition 4 and are shown in Table 10. One national brand also contained activated charcoal.

TABLE 10

Comparison of Nanocomposite to Brand Cat Litter for Ammonia Removal

| Material Evaluated | Ammonia (ppm) | | |
|---|---|---|---|
| | 12 min | 40 min | 90 min |
| Nanocomposite | 35.7 | 1 | 1 |
| Brand A | 74.7 | 41.3 | 23 |
| Brand B | 91.3 | 26 | 10.7 |
| Brand C | 69.3 | 27.3 | 21 |
| Brand D | 49.3 | 19.3 | 0 |
| Brand E | 64.3 | 37 | 25.7 |
| Brand F | 100 | 100 | 67 |

Test Example 9—Nanocomposite Malodor Control on Human Cadavers

A low decomposition nanocomposite was constructed with a 30/30/10/30 ratio by weight of 1) reactive fumed silica nanoparticle subassemblies, 2) amorphous synthetic faujasite nanostructure subassemblies, are preformed spherical ceramic clathrate (as used in Example 5 for desiccating purposes), 3) synthetic zeolite Y and 4) a bulk clay filler, bentonite. The low decomposition formulations may be used, for example, directly on a body to prepare the body for presentation immediately following passing.

A high decomposition nanocomposite was constructed with a 20/50/10/30 ratio of the same components described above to afford higher torso adhesion under conditions of advanced decomposition was applied in excess to cadavers undergoing severe putrefaction weeks after passing. Both the low decomposition and high decomposition nanocomposites demonstrated effective malodor control when used as described exhibiting both excellent torso adhesion and reduction of cadaverine levels over time. Visual observation showed surface adhesion relative to the amount applied. There was a noticeable reduction in odor.

For use, for example, in sealed sachets for use in open or closed caskets or for internment, a nanocomposite was constructed with a 50/50 ratio of reactive fumed silica nanoparticle subassemblies and amorphous synthetic faujasite nanostructure subassemblies admixed in a 17/79/4 weight ratio with a granular blend of three structurally and functionally different activated carbons to assist in gaseous draw within the closed system, and natural clinoptilolite as bulk filler. These sachets were 5×8 inches as a head pillow or 8×14 inches as a torso drape. The sachets were filled to overflowing. Sachets of varying size were evaluated depending upon the need and all proved effective at malodor reduction and maintenance of such over up to three days until internment.

Test Example 10—Nanocomposite Malodor Control in Open Wounds

Nanocomposites were constructed with a 60/38/2 weight ratio of reactive fumed silica nanoparticles, amorphous faujasite nanostructure subassemblies, and a preformed spherical ceramic clathrate (ATS) available from BASF with low affinity for calcium. The preformed spherical ceramic clathrate was used for moisture control in the scab (as humectants). Nanocomposites constructed as such showed excellent mixed clathrate formation in situ in both fresh (bleeding) and debrided wounds in both animals and humans. Nanocomposites were evaluated for effectiveness with hundreds of abrasions, avulsions, lacerations and skin punches and no evidence of wound malodor or infection occurred up to the point of scab loss and healing. The nanocomposites also proved very effective for hemostatic control for both venous and minor arterial bleeding with most bleeding effectively stopped in 30-60 seconds. It was also determined that the nanocomposites were capable of triple component mixed clathrate formation and hemostasis in vitro utilizing blood samples drawn with common anticoagulants as well as in animals undergoing heparin therapy. Human volunteers who were on therapeutic regimens of blood thinning agents and anti-coagulants also showed accelerated hemostasis from an average of 12 minutes (control) to less than 45 seconds (with nanocomposite).

Test Example 11—Nanocomposites for Body Malodor Control

Nanocomposite blends were constructed using 1/99 to 99/1 including 25/75, 40/60, 50/50, 10/40 and 75/25 reactive fumed silica nanoparticles compounded with amorphous synthetic faujasite nanostructure subassemblies as described in Example 6. Following formation and stabilization of the initial nanocomposite blends, nanocomposites were formulated as dry spray deodorants (for example, nanocomposite blend (50/50 ratio) coupled with 1,1-difluoroethane (hydrofluorocarbon 152A) and butane as needed for propulsion) and dry stick deodorants (nanocomposite blend (40/60 ratio) coupled with varying concentrations of cyclomethicone, cyclopentasiloxane, dimethicone, glycerol stearate, lecithin, and glycerol in various ratios. All formulations were effective as deodorants when tested on healthy male and female adult volunteers. In all cases, nanocomposite formulations kept individuals drier (as an antiperspirant) for up to two days duration. For six male volunteers, the nanocomposite formulation under the right arm (three each) or left arm (three each) and with a competitive brand under the other arm were applied once and observations were made for two days by nose every 4 hours except during sleep. This eliminated olfactory-sensed malodor for up to two days duration, and inhibited microbial growth when compared to a leading commercial brand containing alumina zirconia trichlorohydrex.

The invention claimed is:

1. A composition that spontaneously forms a supramolecular mixed host clathrate that entraps desired guest moieties,
   which composition comprises at least first and second components that are different from each other, are hydrophilic and are spontaneously self-assembling to form an asymmetric intercalated lattice framework, wherein when contacted with potential guest moieties said composition forms nanocages that are conformationally mimetic and antisymmetric to said guest moieties,
   wherein said first component has a surface area of at least 380 $m^2/g$ and >8 functional reactive hydrogen-bonding groups per $nm^2$, and
   wherein the second component has a surface area of at least 425 $m^2/g$; and
   wherein the first component is reactive fumed silica and the second component is a synthetic or natural zeolite Y, faujasite or mordenite.

2. The composition of claim 1 which is a powder.

3. The composition of claim 1 wherein the second component is synthetic zeolite Y.

4. A composition which comprises a first component of reactive fumed silica nanoparticle subassemblies with a surface area of at least 380 $m^2/g$ and a second component which is synthetic or natural zeolite Y, faujasite or mordenite, with a surface area of at least 425 $m^2/g$.

5. The composition of claim 4 wherein the second component is synthetic zeolite Y.

6. The supramolecular mixed clathrate of claim 1 containing guest moieties, wherein said guest moieties comprise molds, algae, or spores.

7. The supramolecular mixed clathrate of claim 4 containing guest moieties, wherein said guest moieties comprise molds, algae, or spores.

* * * * *